(12) United States Patent
Taguchi

(10) Patent No.: US 10,073,947 B2
(45) Date of Patent: Sep. 11, 2018

(54) INFORMATION PROCESSING APPARATUS AND IMAGE PROCESSING METHOD

(71) Applicant: Oki Data Corporation, Tokyo (JP)

(72) Inventor: Ayumi Taguchi, Tokyo (JP)

(73) Assignee: Oki Data Corporation, Tokyo (JP)

( * ) Notice: Subject to any disclaimer, the term of this patent is extended or adjusted under 35 U.S.C. 154(b) by 0 days.

(21) Appl. No.: 15/355,797

(22) Filed: Nov. 18, 2016

(65) Prior Publication Data

US 2017/0154155 A1 Jun. 1, 2017

(30) Foreign Application Priority Data

Nov. 30, 2015 (JP) ................................. 2015-233518

(51) Int. Cl.
| | | |
|---|---|---|
| *H04N 1/40* | (2006.01) | |
| *G06K 15/00* | (2006.01) | |
| *H04N 1/60* | (2006.01) | |
| *G06F 19/00* | (2018.01) | |
| *H04N 1/00* | (2006.01) | |
| *G06K 15/02* | (2006.01) | |
| *A61B 6/00* | (2006.01) | |

(52) U.S. Cl.
CPC .......... *G06F 19/321* (2013.01); *A61B 6/5211* (2013.01); *G06K 15/188* (2013.01); *H04N 1/00204* (2013.01); *H04N 1/00244* (2013.01); *H04N 1/6027* (2013.01); *H04N 2201/0082* (2013.01); *H04N 2201/0094* (2013.01)

(58) Field of Classification Search
CPC ... G06F 19/321; A61B 6/5211; G06K 15/188; H04N 1/00204; H04N 1/00244; H04N 1/6027; H04N 2201/0082; H04N 2201/0094

USPC ........................................ 358/3.24, 1.9, 1.15
See application file for complete search history.

(56) References Cited

U.S. PATENT DOCUMENTS

| | | | |
|---|---|---|---|
| 6,912,061 B1 | 6/2005 | Ozaki | |
| 2013/0177222 A1* | 7/2013 | Tridandapani | A61B 5/1171 382/128 |
| 2015/0100787 A1* | 4/2015 | Westin | G06F 21/602 713/168 |

FOREIGN PATENT DOCUMENTS

| | | |
|---|---|---|
| JP | 2001094714 A | 4/2001 |
| JP | 2015-126301 | 7/2015 |

\* cited by examiner

*Primary Examiner* — Quang N Vo

(74) *Attorney, Agent, or Firm* — Panitch Schwarze Belisario & Nadel LLP

(57) ABSTRACT

An information processing apparatus includes: a storage unit that stores determination information in which for each of a plurality of types of modalities that each generate medical information data including medical image data and type data indicating the type of the modality, method information indicating a color conversion method for the medical image data is associated with type data indicating the type of modality; a data receiver that receives data; a data acquisition unit that, when the received data is medical information data, acquires the type data from the received data; a method determiner that determines, based on the acquired type data and the determination information stored in the storage unit, the color conversion method for the medical image data included in the received data; and a color converter that performs color conversion on the medical image data according to the determined color conversion method to generate print image data.

23 Claims, 9 Drawing Sheets

FIG. 5

| TAG (29) | ATTRIBUTE NAME | VR (30) | MEANING OF VR | DATA BODY (32) |
|---|---|---|---|---|
| (0008, 0020) | EXAMINATION DATE | DA | Date | 20150722 |
| (0008, 0030) | EXAMINATION TIME | TM | Time | 171520 |
| (0008, 0060) | MODALITY | CS | Code String | MODALITY CODE |
| (0010, 0010) | PATIENT'S NAME | PN | Person Name | XXX^XXX |
| (0010, 0020) | PATIENT'S ID | LO | Long String | 123456 |
| (7FE0, 0010) | PIXEL INFORMATION | OB | Other Byte String | PIXEL DATA |
| ... | ... | ... | ... | ... |

| NAME OF MODALITY | MODALITY CODE | COLOR CONVERSION METHOD |
|---|---|---|
| COMPUTED X-RAY IMAGING DEVICE | CR | K MONOCHROME CONVERSION |
| COMPUTED TOMOGRAPHY DEVICE | CT | CMYK COLOR CONVERSION |
| MAMMOGRAPHY DEVICE | MG | K MONOCHROME CONVERSION |
| NUCLEAR MAGNETIC RESONANCE TOMOGRAPHY DEVICE | MR | CMYK COLOR CONVERSION |
| ULTRASONIC DIAGNOSTIC DEVICE | US | CMYK COLOR CONVERSION |
| OTHER MODALITIES | — | CMYK COLOR CONVERSION |

INFORMATION PROCESSING APPARATUS AND IMAGE PROCESSING METHOD

BACKGROUND OF THE INVENTION

1. Field of the Invention

The present invention relates to an information processing apparatus and an image processing method.

2. Description of the Related Art

Recently, various diagnostic imaging devices referred to as modalities are used as medical diagnostic devices in medical practice. The modalities include ultrasonic diagnostic devices, nuclear magnetic resonance tomography devices, computed tomography devices, computed x-ray imaging devices, and the like. These various modalities read regions to be diagnosed of patients to generate medical image data. Based on medical image data generated by modalities, color printers form, on surfaces of film media, print images, which are used for examination or diagnosis by physicians.

Japanese Patent Application Publication No. 2001-94714 discloses a network system including a workstation that acquires medical image data from a modality and performs gradation processing corresponding to the modality on the medical image data, and a printer that forms a print image on a surface of a film medium based on the medical image data.

Print images formed on surfaces of film media based on medical image data are familiar to physicians who use the print images for examination or diagnosis. However, in some cases, such print images are hard to see for patients and their families who know little about medical care and are unfamiliar with them. Thus, recently, in some oases, a print image is formed on a surface of a paper medium based on medical image data by a color printer and used by a physician for explaining the diagnosis to a patient and his or her family.

SUMMARY OF THE INVENTION

An aspect of the present invention is intended to provide an information processing apparatus and an image processing method capable of appropriately performing color conversion on medical image data.

According to an aspect of the present invention, there is provided an information processing apparatus comprising: a storage unit that stores color conversion method determination information in which for each of a plurality of types of modalities that each generate medical information data including medical image data and modality type data indicating the type of the modality, color conversion method information indicating a color conversion method for the medical image data is associated with modality type data indicating the type of modality; a data receiver that receives data; a data acquisition unit that, when the data received by the data receiver is medical information data, acquires the modality type data from the received medical information data; a method determiner that determines, based on the modality type data acquired by the data acquisition unit and the color conversion method determination information stored in the storage unit, the color conversion method for the medical image data included in the received medical information data; and a color converter that performs color conversion on the medical image data according to the color conversion method determined by the method determiner to generate print linage data.

According to another aspect of the present invention, there is provided an image processing method comprising: receiving data; acquiring, when the received data is medical information data generated by a modality and including medical image data, modality type data indicating a type of the modality from the received medical information data; determining, based on the acquired modality type data and color conversion method determination information in which for each of a plurality of types of modalities that each generate medical information data including medical image data, color conversion method information indicating a color conversion method for the medical image data is associated with modality type data indicating the type of modality, the color conversion method for the medical image data included in the received medical information data; and performing color conversion on the medical image data according to the determined color conversion method to generate print image data.

BRIEF DESCRIPTION OF THE DRAWINGS

In the attached drawings:

FIG. 5 is a schematic diagram for explaining data stored in the metadata section;

FIG. 8 is a schematic diagram illustrating a configuration of a color conversion method determination table;

DETAILED DESCRIPTION OF THE INVENTION

An embodiment of the present invention will now be described with reference to the attached drawings.

(1) Embodiment (1-1) Configuration of Image Forming System

Figure 1:
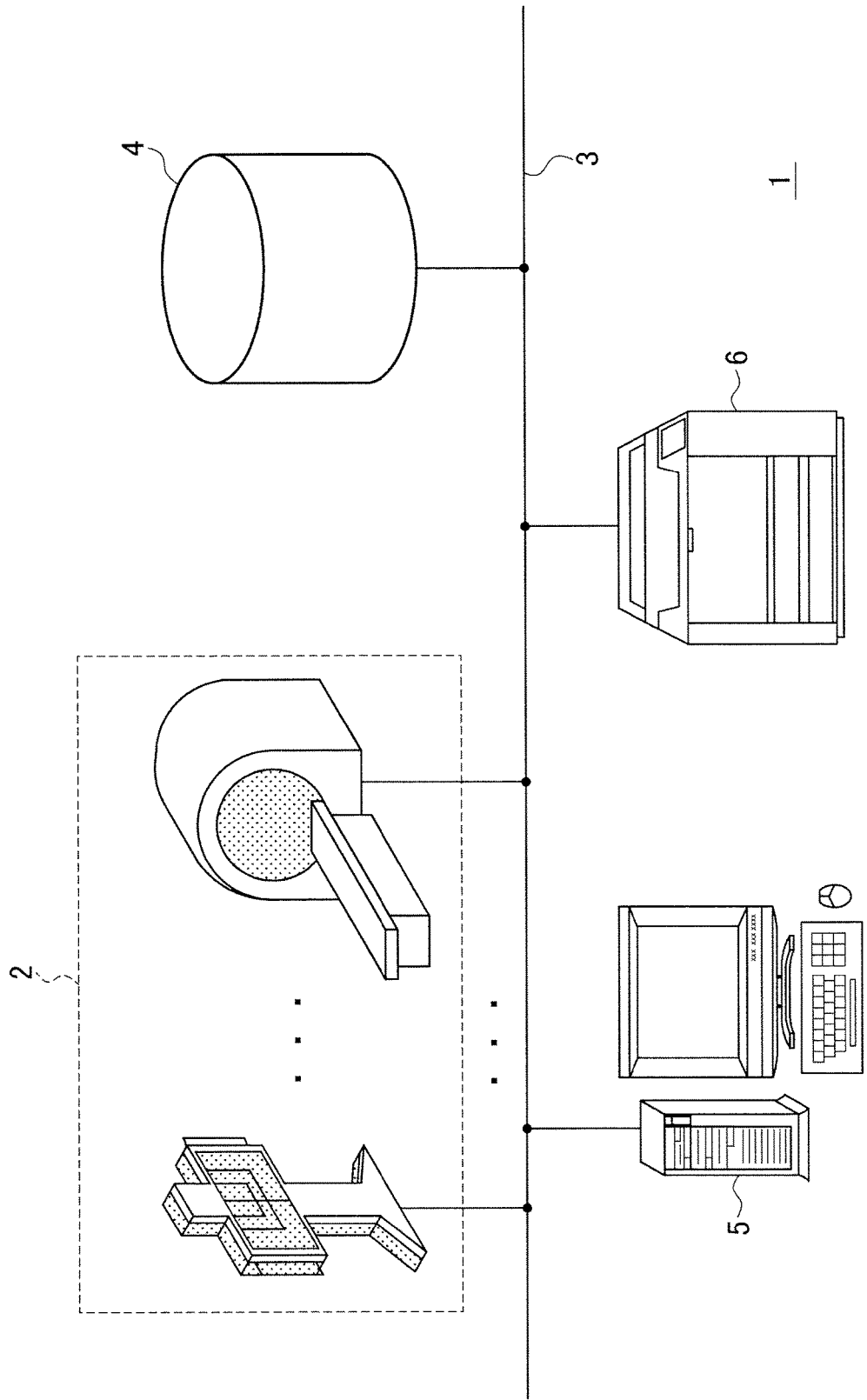
FIG. 1 is a block diagram illustrating a configuration of an image forming system according an embodiment.

FIG. 1 illustrates an image forming system 1 according to the embodiment. The image forming system 1 includes various modalities 2, such as a computed X-ray imaging device, a computed tomography device, a mammography device, a nuclear magnetic resonance tomography device, and an ultrasonic diagnostic device, an image server 4, a personal computer 5, and a color printer 6 as an image forming apparatus or information processing apparatus, which are connected to each other via a network 3. The color printer 6 is, for example, a color electrophotographic printer.

Each of the various modalities 2 reads a region to be diagnosed of a patient to generate medical image data in Red-Green-Blue (RGB) format, and generates file data (also referred to below as DICOM file data) in Digital Imaging and Communication in Medicine (DICOM) format including the medical image data. The DICOM format is specified for transmitting medical image data via networks and storing medical image data in image servers. Each of the various modalities 2 transmits DICOM file data to the image server 4 via the network 3 to store the DICOM file data in the image server 4, and transmits DICOM file data to the personal computer 5 or color printer 6.

The personal computer 5 acquires DICOM file data from the various modalities 2 and image server 4 and stores the DICOM file data as appropriate, and processes the medical image data in the DICOM file data as appropriate. The personal computer 5 transmits the DICOM file data with the medical image data processed as appropriate to the image server 4 via the network 3 to store the DICOM file data in the image server 4, and also transmits the DICOM file data to the color printer 6. The personal computer 5 converts image data of an image to be printed consisting of characters, figures, or the like into commands written in a page description language (PDL) that can be interpreted by the color printer 6, and generates print data including the commands. The personal computer 5 may transmit the print data to the color printer 6 via the network 3.

The color printer 6 receives DICOM file data that is generated according to the DICOM standard and transmitted from the modalities 2 or personal computer 5, and prints the medical image data in the DICOM file data. The color printer 6 also receives DICOM file data transmitted directly from the image server 4 by the personal computer 5, and prints the medical image data in the DICOM file data. When print data is transmitted from the personal computer 5, the color printer 6 may receive the print data and print the image data of the image to be printed in the print data.

(1-2) Circuit Configuration of Modality

A basic circuit configuration common to the various modalities 2 will be novo be described with reference to FIG. 2. Each of the modalities 2 includes a controller 10, such as a central processing unit (CPU) or a microprocessor. Each of the modalities 2 also includes a storage unit 11, such as a hard disk drive or a read only memory (ROM), an operation unit (or user interface) 12 including operation keys, a touch panel, or the like operated by an operator, a reading unit (or imaging unit) 13, and a transmitter 14, which are connected to the controller 10.

The controller 10 reads and expands, in a random access memory (RAM) in the controller 10, various programs, such as a basic program and a DICOM file generating program, previously stored in the storage unit 11, as appropriate. The controller 10 controls the entire modality 2 in accordance with the various programs expanded in the RAM and executes various processes to provide various functions in cooperation with the reading unit 13 and transmitter 14.

Figure 2:
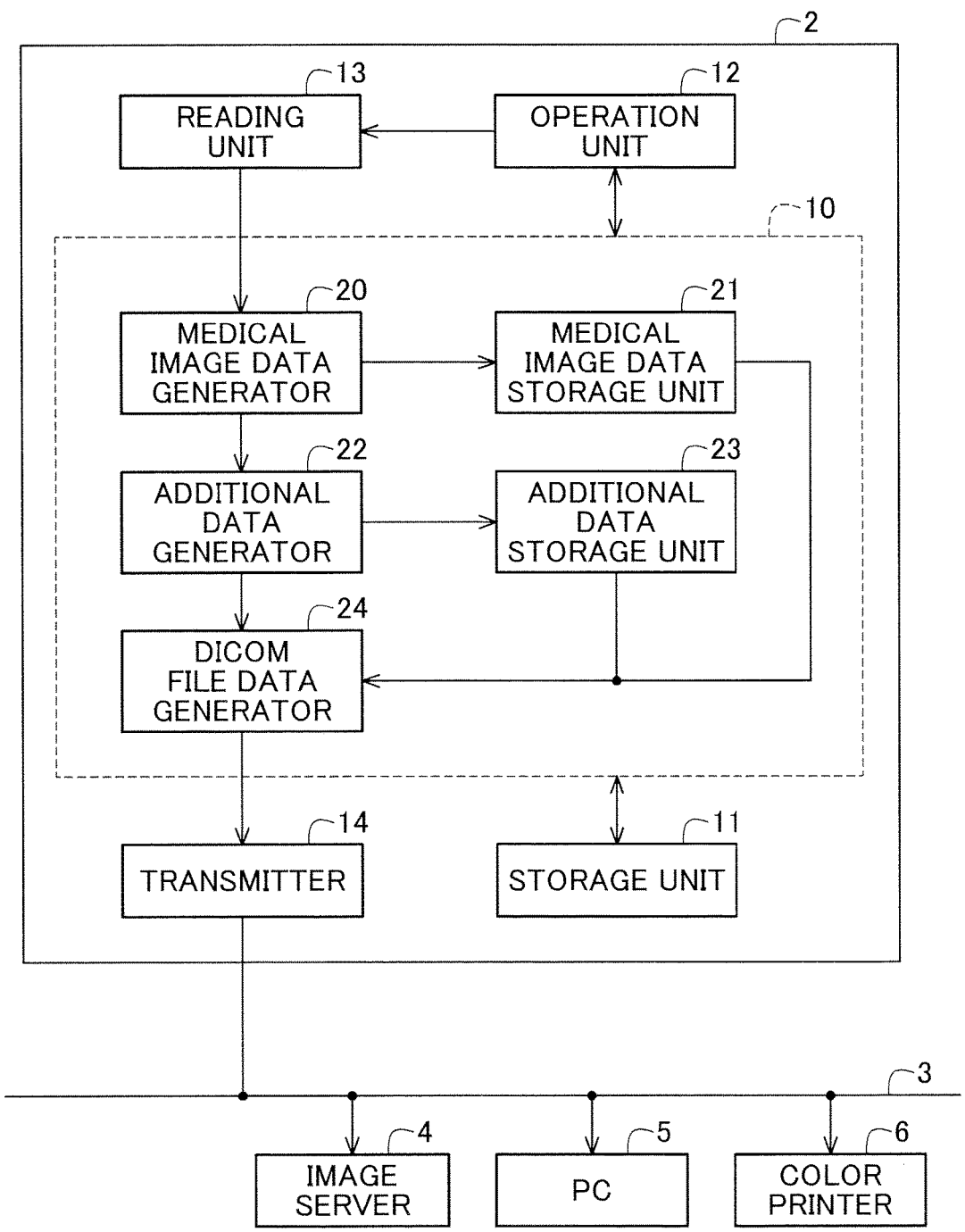
FIG. 2 is a block diagram illustrating a circuit configuration of a modality.

For the sake of convenience, FIG. 2 illustrates the various functions provided by the controller 10 in accordance with the various programs as functional circuit blocks. The various processes executed by the controller 10 in accordance with the various programs will be described as processes executed by the respective functional circuit blocks. The modality 2 may be configured so that it includes hardware circuit blocks capable of executing the same processes as the functional circuit blocks described below and executes the various processes executed by the controller 10 by means of the hardware circuit blocks.

The controller 10 includes a medical image data generator 20, a medical image data storage unit 21, an additional data generator 21, an additional data storage unit 13, and a DICOM file data generator 24.

When the reading unit 13 receives a reading instruction from the operation unit 12, it reads a region to be diagnosed of a patient by a predetermined reading method, such as photographing or scanning, using X-rays, magnetism, ultrasonic waves, or the like, depending on the function of the modality 2, to generate read data, and sends it to the medical image data generator 20. The medical image data generator 20 generates, based on the read data from the reading unit 13, medical image data in RGB format representing the region to be diagnosed of the patient. The medical image data generator 20 then sends the medical image data to the medical image data storage unit 21, which is, for example, the RAM in the controller 10, to store the medical image data in the medical image data storage unit 21, and sends image attribute data indicating attributes of the medical image data to the additional data generator 22.

When the additional data generator 22 receives the image attribute data from the medical image data generator 20, it generates additional data to be attached to the medical image data, based on the image attribute data, examination data and patient data input through the operation unit 12 at this time, device data regarding the modality 2 previously stored in the storage unit 11, and the like. The additional data generator 22 then sends the additional data to the additional data storage unit 23, which is the RAM in the controller 10, to store the additional data in the additional data storage unit 23, and notifies the DICOM file data generator 24 that the additional data has been stored in the additional data storage unit 23. When the DICOM file data generator 24 receives the notification from the additional data generator 22, in response to this, it reads the medical image data from the medical image data storage unit 21 and reads the additional data from the additional data storage unit 23. The DICOM file data generator 24 then generates DICOM file data including the medical image data and additional data.

Figure 3:
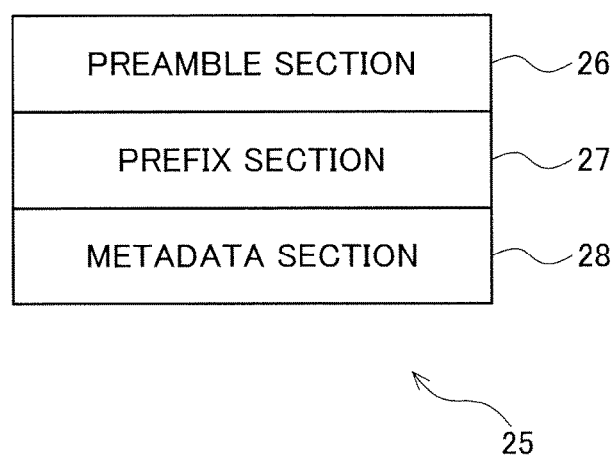
FIG. 3 is a schematic diagram illustrating a configuration of DICOM file data.

As illustrated in FIG. 3, DICOM file data 25 includes a preamble section 26, a prefix section 27, and a metadata section 28. The preamble section 26 is a header of the DICOM file data. The prefix section 27 includes DICOM identification data that is a character string of "DICM" indicating the DICOM file data 25. Thus, the prefix section 27 allows a receiver of the DICOM file data to determine, from the DICOM identification data, that the received data is DICOM file data.

Figure 4:
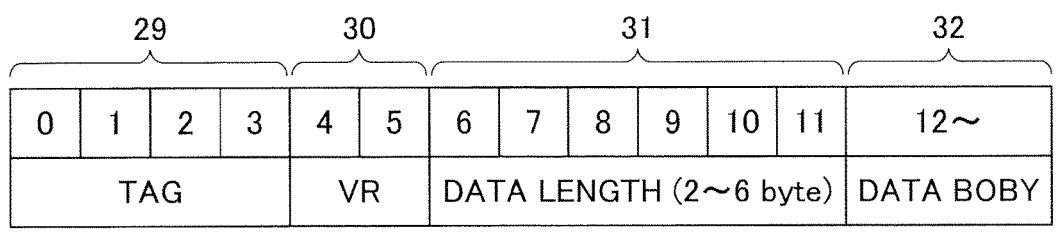
FIG. 4 is a schematic diagram illustrating a configuration of a metadata section.

As illustrated in FIG. 4, the metadata section 28 includes a tag storage section 29, a value representation (VR) storage section 30, a data length storage section 31, and a data body storage section 32. The metadata section 28 stores multiple intended data items. For each of the intended data items, tag data assigned to the intended data item, VR data indicating the type of the intended data item, length data indicating the length of the intended data item, and the intended data item itself are respectively stored in the tag storage section 29, VR storage section 30, data length storage section 31, and data body storage section 32 in association with each other.

The metadata section 28 will be specifically described with reference to FIG. 5. The metadata section 28 stores, as the intended data items, examination date data indicating the date of an examination of a patient, examination time data indicating the time of the examination of the patient, a modality code, patient name data indicating the name of the patient, patient identification data capable of individually identifying the patient, medical image data consisting of multiple pixel values, and other data (not specifically illustrated in FIG. 5), such as a variety of image attribute data of the medical image data. Each of the intended data items is stored in the metadata section 28 together with the corresponding tag data, VR data, and length data (not illustrated in FIG. 5). The modality code is modality type data indicating the type of modality.

Of the data stored in the metadata section 28, the data other than the medical image data is the additional data described above. The tag data for each intended data item has an attribute name corresponding thereto on a one-on-one basis. To facilitate understanding of the metadata section 28, FIG. 5 illustrates, for each intended data item, the attribute name of the tag data and the meaning of the VR data, which are not actually stored in the metadata section 28. The DICOM standard specifies that if the type (i.e., VR) of data can be determined from the tag data, the VR data corresponding to the tag data need not be stored in the metadata section 28.

When the DICOM file data generator 24 generates DICOM file data as illustrated in FIGS. 3 to 5, it sends the DICOM file data to the transmitter 14. The transmitter 14 transmits the DICOM file data to a destination (the image server 4, personal computer 5, or color printer 6) designated through the operation unit 12 at this time.

(1-3) Configuration of Color Printer

Figure 6:
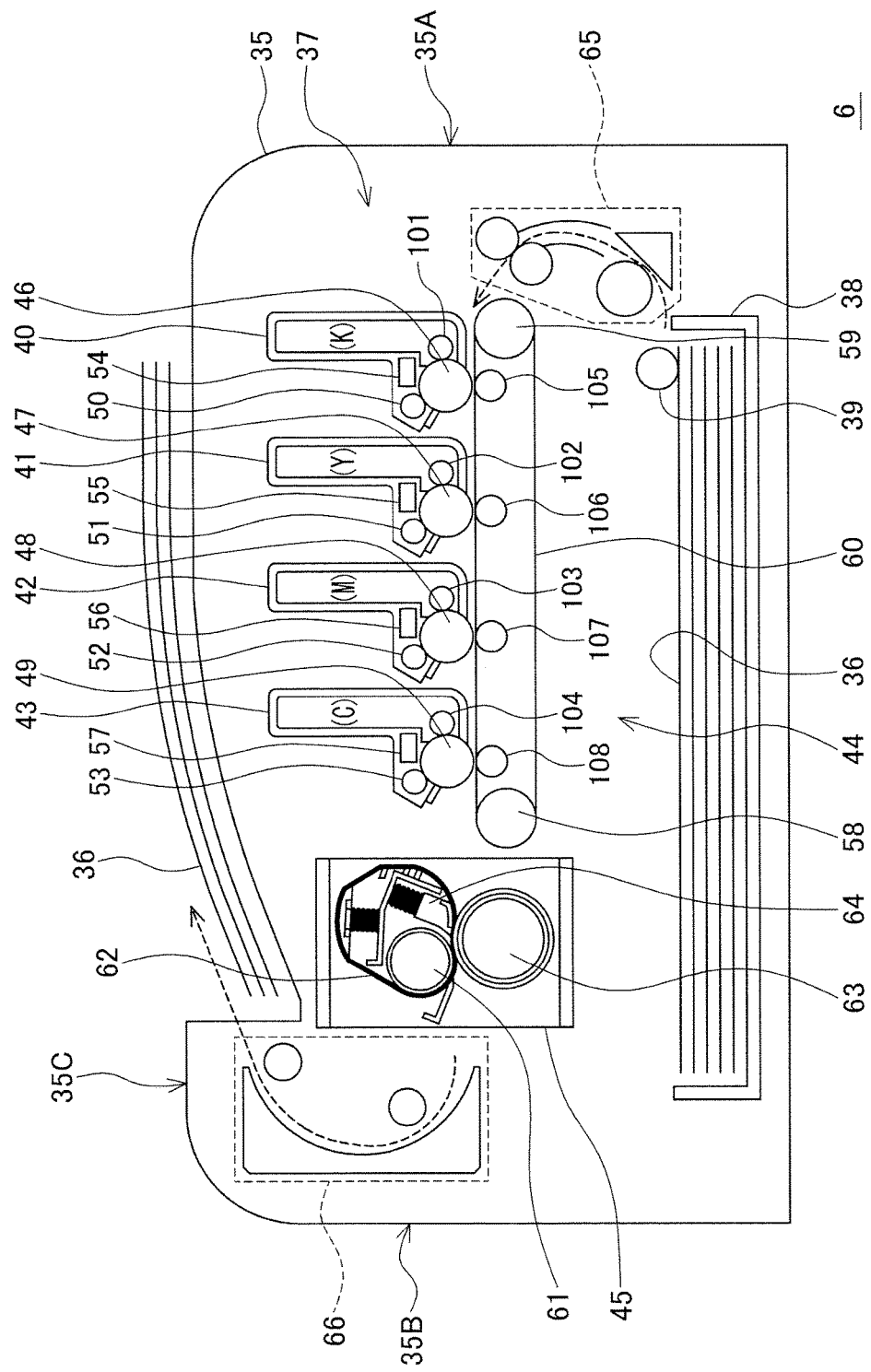
FIG. 6 is a schematic cross-sectional, diagram illustrating a configuration of a color printer.

Next, a configuration of the color printer 6 will be described with reference to FIG. 6. The color printer 6 includes, for example, a substantially box-shaped printer housing 35 with a front surface 35A on the right side of FIG. 6 and a back surface 35B on the left side of FIG. 6. In the central part of the printer housing 35 is disposed an image forming section 37 that forms a print image on a surface of a white paper medium (or a print medium) 36. In the lower part of the printer housing 35 are disposed a medium cassette 38 that stores multiple paper media 36 and a feed roller 39 that feeds one by one the paper media 36 from the medium cassette 38.

The image forming section 37 includes first to fourth image forming units 40 to 43, a transfer unit 44, and a fixing unit 45. Each of the image forming units 40 to 43 uses toner as developer to form a toner image as a developer image from which a print image is to be formed. The image forming units 40, 41, 42, and 43 use toners of black (K), yellow (Y), magenta (M), and cyan (C), respectively. The image forming units 40 to 43 include photosensitive drums 46 to 49, charging rollers 50 to 53, developing units 101 to 104, and light emitting diode (LED) heads 54 to 57.

The transfer unit 44 includes a belt drive roller 58, a driven roller 59, and an endless transfer belt 60 stretched around the belt drive roller 58 and driven roller 59, and four transfer rollers 103 to 108 pressed against the photosensitive drums 46 to 49 of the image forming units 40 to 43 with the transfer belt 60 therebetween. The fixing unit 45 fixes toner images on a surface of a paper medium 36 by applying heat and pressure to the toner images, forming a print image. The fixing unit 45 includes a fixing roller 61, an endless heating belt 62 stretched around a belt tension member 64, and a pressure roller 63 pressed against the heating belt 62. The fixing unit 45 also includes a heater (not illustrated) in the heating belt 62.

In addition, in the front surface 35A side of the printer housing 35 is disposed a medium supply conveying unit 65. The medium supply conveying unit 65 includes multiple pairs of conveying rollers, a conveying guide, and the like, and conveys a paper medium 36 from the medium cassette 38 to the image forming section 37 via a supply conveying path. Also, in the back surface 35B side of the printer housing 35 is disposed a medium discharge conveying unit 66. The medium discharge conveying unit 66 includes multiple pairs of conveying rollers, a conveying guide, and the like, and conveys and discharges a paper medium 36 from the fixing unit 45 to a stacker formed by a top surface 35C of the printer housing 35 via a discharge conveying path.

The color printer 6 includes a controller 70, described later, in the printer housing 35. When forming a color print image, the controller 70 drives and controls portions in the printer housing 35, thereby feeding the paper media 36 one by one from the medium cassette 38 to the image forming section 37 through the supply conveying path. At this time, the controller 70 sequentially controls the LED heads 54 to 57 of the image forming units 40 to 43 in accordance with black, cyan, magenta, and yellow color components of a color print image to be formed. The controller 70 causes the image forming units 40 to 43 to charge surfaces of the photosensitive drums 45 to 49 by the charging rollers 50 to 53, expose the surfaces to form electrostatic latent images on the surfaces by the LED heads 54 to 57, and develop the electrostatic latent images with toner by the developing units 101 to 104 to form toner images.

The controller 70 also causes the transfer unit 44 to sequentially transfer the toner images on the surfaces of the four photosensitive drums 46 to 49 onto a surface of the paper medium 36 conveyed to the image forming section 37 in a superposed manner by the four transfer rollers 105 to 108 while conveying the paper medium 36 by the transfer belt 60. The controller 70 then causes the fixing unit 45 to apply heat and pressure to the paper medium 36 by the heating belt 62 and pressure roller 63 while nipping and conveying the paper medium 36 by the heating belt 62 and pressure roller 63, thereby fixing the toner images of the four colors to the surface of the paper medium 36 to form a color print image. The controller 70 then conveys and discharges the paper medium 36 to the stacker through the discharge conveying path.

When forming a monochrome print image, the controller 70 drives and controls portions in the printer housing 35, thereby feeding the paper media 36 one by one from the medium cassette 38 to the image forming section 37 through the supply conveying path in the same manner as above. At this time, the controller 70 controls the LED head 54 of the first image forming unit 40 in accordance with a black color component of a monochrome print image to be formed. The controller 70 causes only the first image forming unit 40 to charge the surface of the photosensitive drum 46 by the charging roller 50, expose the surface by the LED head 54 to form an electrostatic latent image on the surface, and develop the electrostatic latent image with toner by the developing unit 101 to form a toner image.

The controller 70 also causes the transfer unit 44 to transfer the toner image on the surface of the photosensitive drum 46 onto a surface of the paper medium 36 conveyed to the image forming section 37 by the transfer roller 105 while conveying the paper medium 36 by the transfer belt 60. The controller 70 then causes the fixing unit 45 to apply heat and pressure to the paper medium 36 by the heating belt 62 and pressure roller 63 while nipping and conveying the paper medium 36 by the heating belt 62 and pressure roller 63, thereby fixing the toner image of the single color to the surface of the paper medium 36 to form a monochrome print image. The controller 70 then conveys and discharges the paper medium 36 to the stacker through the discharge conveying path.

As such, the controller 70 can form a color print image and a monochrome print image on surfaces of paper media 36.

(1-4) Circuit Configuration of Color Printer

Next, a circuit configuration of the color printer 6 will be described with reference to FIG. 7. The color printer 6 includes the controller 70, such as a CPU or a microprocessor, a storage unit 71, such as a hard disk drive or a ROM, and a data receiver 72. The controller 70 is connected to the storage unit 71, data receiver 72, and LED heads 54 to 57. Although not illustrated, the controller 70 is also connected to motors, power supplies, and other components, for causing the image forming section 37, medium discharge conveying unit 66, and medium supply conveying unit 65 to operate when forming a print image on a surface of a paper medium 36.

The controller 70 reads and expands, in a RAM in the controller 70, various programs, such as a basic program and an image processing program, previously stored in the storage unit 71, as appropriate. The controller 70 controls the entire color printer 6 in accordance with the various programs expanded in the RAM and executes various processes to provide various functions in cooperation with the data receiver 72, LED heads 54 to 57, and other components.

Figure 7:
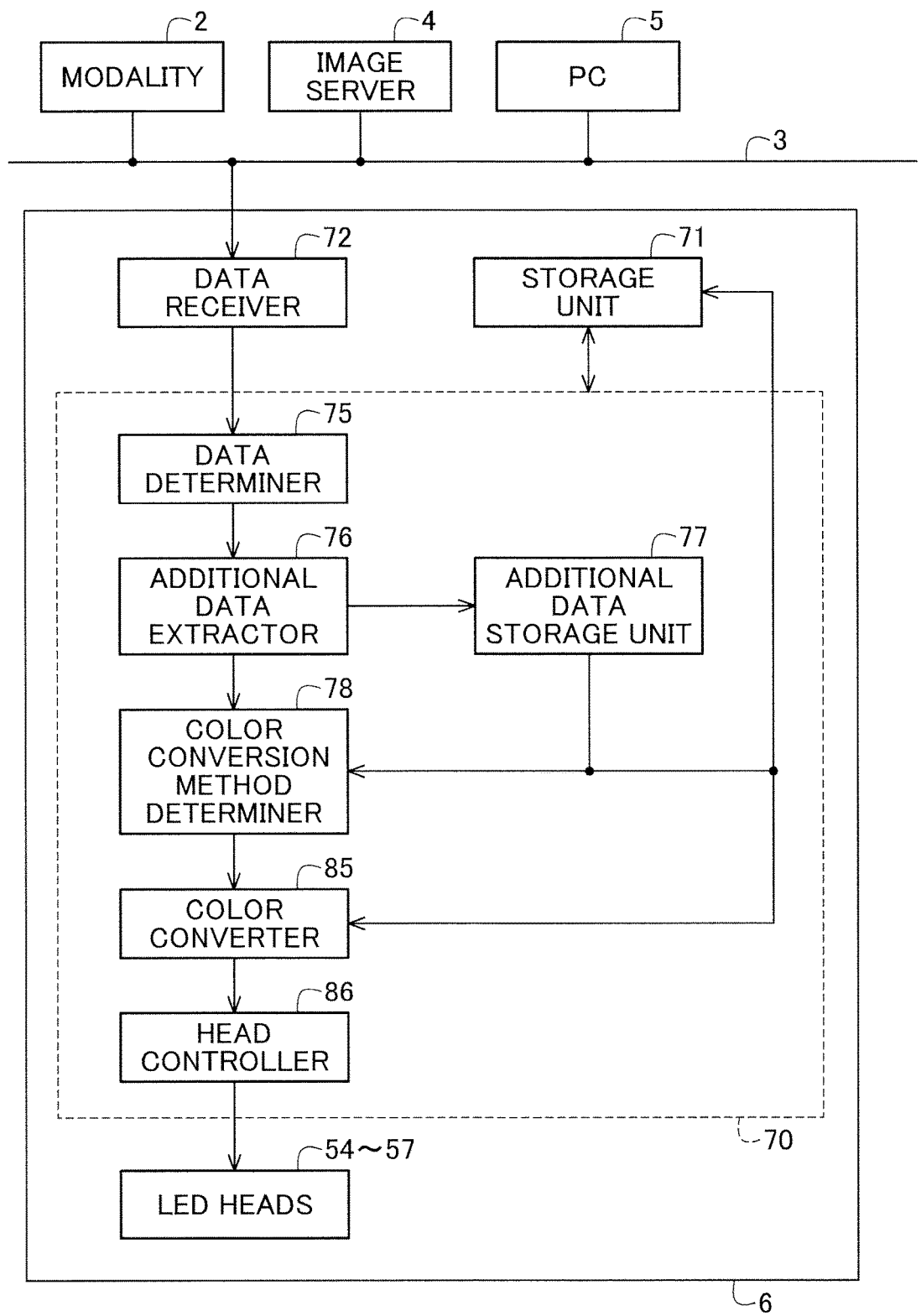
FIG. 7 is a block diagram illustrating a circuit configuration of the color printer.

For the sake of convenience, FIG. 7 illustrates the various functions provided by the controller 70 in accordance with the various programs as functional circuit blocks. The various processes executed by the controller 70 in accordance with the various programs will be described as processes executed by the respective functional circuit blocks. The color printer 6 may be configured so that it includes hardware circuit blocks capable of executing the same processes as the functional circuit blocks described below and executes the various processes executed by the controller 70 by means of the hardware circuit blocks.

The controller 70 includes a data determiner 75, an additional data extractor 76, an additional data storage unit 77, a color conversion method determiner 78, a color converter 35, and a head controller 86.

When DICOM file data, is transmitted from a modality 2, the personal computer 5, or the image server 4 through the network 3, the data receiver 72 receives the DICOM file data and sends it to the data determiner 75. When print data is transmitted from the personal computer 5 through the network 3, the data receiver 72 receives the price data and sends it to the data determiner 75.

When the data determiner 75 receives data, which is DICOM file data or print data, from the data receiver 72, it analyzes the received data to determine whether the received data is DICOM file data. Specifically, when the data determiner 75 detects that the received data includes the DICOM identification data described above, it determines that the received data is DICOM file data. The data determiner 75 then sends the DICOM file data to the additional data extractor 76.

When the additional data extractor 76 receives the DICOM file data from the data determiner 75, it extracts the additional data and medical image data from the DICOM file data. The additional data extractor 76 then sends the additional data to the additional data storage unit 77, which is the RAM in the controller 70, to store the additional data in the additional data storage unit 77, and sends the medical image data to the color conversion method determiner 78. When the color conversion method determiner 78 receives the medical image data from the additional data extractor 76, it reads the additional data from the additional data storage unit 77 and acquires the modality code from the additional data.

As illustrated in FIG. 8, the storage unit 71 stores a color conversion method determination table 80 that is a data table as color conversion method determination information for determining a color conversion method used for color conversion of medical image data in RGB format in accordance with the type of the modality 2 that is the generation source of the medical image data. The color conversion method determination table 80 describes, for each, type of modality, device name data 81 indicating the name of the type of modality, the modality code 82, and color conversion method information 83 indicating a color conversion method in association with each other, for example.

In this embodiment, as a color conversion method, there is a K monochrome conversion method for performing color conversion on medical image data in RGB format to generate print image data in K format representing the medical image data by a single color of black (K). Also, as another color conversion method, there is a CMYK color conversion method for performing color conversion on medical image data in RGB format to generate print image data in CMYK format representing the medical image data by colors of cyan (C), magenta (M), yellow (Y), and black (K).

The various modalities 2 include computed X-ray imaging devices and mammography devices (referred to below as X-ray-based modalities) that read regions to be diagnosed of patients using X-rays. In the color printer 6, the K monochrome conversion method is assigned to medical image data of the X-ray-based modalities as a color conversion method for color conversion. The various modalities 2 also include computed tomography devices, nuclear magnetic resonance tomography devices, and ultrasonic diagnostic devices (referred to below as non-X-ray-based modalities) that read regions to be diagnosed of patients without using X-rays. In the color printer 6, the CMYK color conversion method is assigned to medical image data of the non-X-ray-based modalities as a color conversion method for color conversion.

When the color conversion method determiner 78 acquires the modality code from the additional data, it determines, based on the modality code and the color conversion method determination table 80 stored in the storage unit 71, a color conversion method for color conversion to be applied to the medical image data. The color conversion method determiner 78 then sends color conversion method information indicating the determined color conversion method along with the medical image data to the color converter 85.

The storage unit 71 also stores a color conversion table (referred to below as the K color conversion table) that is a look-up table as monochrome conversion information used for color conversion of the K monochrome conversion method. The storage unit 71 also stores a color conversion table (referred to below as the CMYK color conversion table) that is a look-up table as multicolor conversion information used for color conversion of the CMYK color conversion method.

When the color converter 85 receives the color conversion method information along with the medical image data from the color conversion method determiner 78, it reads, from the storage unit 71, one of the K color conversion table and CMYK, color conversion table corresponding to the color conversion method indicated by the color conversion method information. When the color conversion method information indicates the K monochrome conversion method, the color converter 85 reads K color conversion table from the storage unit 71, and then performs color conversion (RGB-to-CMYK color conversion) on the medical image data in RGB format based on the K color conversion table to generate print image data in K format that is monochrome image data representing an image by a single color of K. When the color conversion method information indicates the CMYK color conversion method, the color converter 85 reads CMYK color conversion table from the storage unit 71, and then performs color conversion (RGB-to-CMYK color conversion) on the medical image data in RGB format based on the CMYK color conversion table to generate print image data in CMYK format that is multicolor image data representing an image by multiple colors of C, M, Y, and K. The color converter 85 sends the generated print image data in K or CMYK format to the head controller 86.

When the head controller 86 receives print image data in K format from the color converter 85, it generates one line of head control data in accordance with a black color component based on the print image data, and sends it to the LED head 54 of the first image forming unit 40. The head controller 86 controls the LED head 54 of the first image forming unit 40 based on the one line of head control data to form a medical image in the form of a K print image (i.e., a monochrome print image representing an image by a single, color of black) on a surface of a paper medium 36 in the manner described above.

On the other hand, when the head controller 86 receives print image data in CMYK format from the color converter 85, it generates four lines of head control data in accordance with black, cyan, magenta, and yellow color components based on the print image data, and sends them to the LED heads 54 to 57 of the image forming units 40 to 43. The head controller 86 controls the LED heads 54 to 57 of the image forming units 40 to 43 based on the four lines of head control data to form a medical image in the form of a CMYK print image (i.e., a color print image representing an image by multiple colors of cyan, magenta, yellow, and black) on a surface of a paper medium 36 in the manner described above.

When the data determiner 75 detects that the data supplied from the data receiver 72 includes no DICOM identification data, it determines that the data supplied from the data receiver 72 is print data in PDL format. The data determiner 75 then sends the print data to the color converter 85.

When the color converter 85 receives the print data from the data determiner 75, it reads, depending on whether the image to be printed represented by the print data is monochrome or color, the corresponding one of the K color conversion table and CMYK color conversion table from the storage unit 71. When the image to be printed is monochrome, the color converter 85 reads the K color conversion table from the storage unit 71, and then performs color conversion on the image to be printed represented by the print data based on the K color conversion table to generate print image data in K format. When the image to be printed is color, the color converter 85 reads the CMYK color conversion table from the storage unit 71, and then performs color conversion on the image to be printed represented by the print data based on the CMYK color conversion table to generate print, image data in CMYK format. The color converter 85 sends the generated print image data in K or CMYK format to the head controller 86.

When the head controller 86 receives print image data in K format from the color converter 85, it generates one line of head control data in accordance with a black color component based on the print image data, and sends it to the LED head 54 of the first image forming unit 40. The head controller 86 controls the LED head 54 of the first image forming unit 40 based on the one line of head control data to form a monochrome print image on a surface of a paper medium 36 in the manner described above.

On the other hand, when the head controller 86 receives print image data in CMYK format from the color converter 85, it generates four lines of head control data in accordance with black, cyan, magenta, and yellow color components based on the print image data, and sends them to the LED heads 54 to 57 of the image forming units 40 to 43. The head controller 86 controls the LED heads 54 to 57 of the image forming units 40 to 43 based on the four lines of head control data to form a color print image on a surface of a paper medium 36 in the manner described above.

The assignment of the color conversion methods for color conversion to medical image data in RGB format will now be described. Or the various modalities 2, the X-ray-based modalities generate medical image data of monochrome (or multilevel grayscale) medical images (or X-ray images); non-X-ray-based modalities also generate medical image data of monochrome (or multilevel grayscale) medical images (e.g., tomographic images or the like). Recently, techniques of coloring gray portions in medical images to desired colors have been developing.

However, in medical images generated by the X-ray-based modalities, regions to be diagnosed, such as human bones or internal structures of breasts, are shown as gray portions obtained by reading the regions and occupy almost the entire read images, so they are easy to identify. Thus, regarding medical images generated by line X-ray-based modalities, gray portions are not colored.

Figure 9:
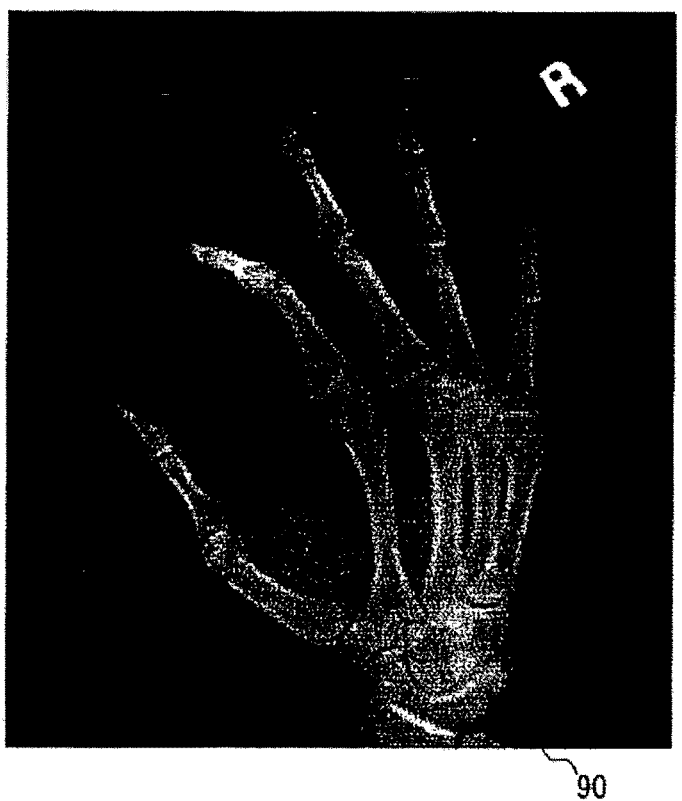
FIG. 9 is a view of a print image formed based on data obtained by performing color conversion on medical image data generated by an X-ray-based modality according to a CMYK color conversion method.

Thus, in the color printer 6, the K monochrome conversion method is assigned to medical image data in RGB format generated by the X-ray-based modalities, as described above. This will be specifically described by taking, as an example, a case of performing color conversion on medical image data in RGB format generated by an X-ray-based modality reading a hand as a region to be diagnosed of a patient with X-rays. FIG. 9 illustrates a print image 90 formed on a surface of a paper medium 36 based on print image data obtained by applying color conversion to the medical image data in RGB format according to the CMYK color conversion method. In the print image 90, portions other than the bones of the hand are faded and the outlines are blurred. Further, the print image 90 shows degradation in brightness and tone in the portions of the bones of the hand, has high transmittance overall, and has poor visibility.

Figure 10:
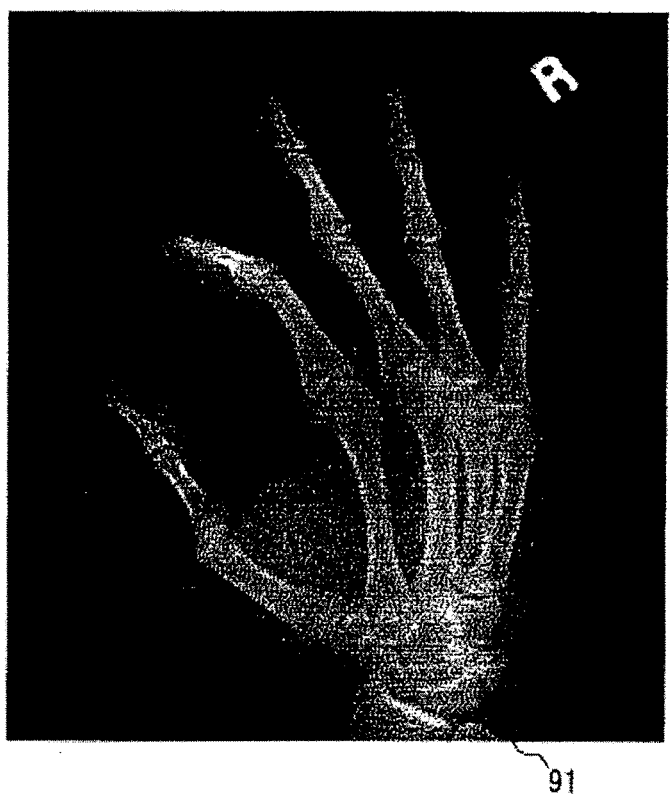
FIG. 10 is a view of a print image formed based on data obtained by performing color conversion on medical image data generated by an X-ray-based modality according to a K monochrome conversion method.

FIG. 10 illustrates a print image 91 formed on a surface of a paper medium 36 based on print image data obtained by applying color conversion to the medical image data in RGB format according to the K monochrome conversion method. In the print image 91, portions other than the bones of the hand are not faded, the outlines are clear, and wrinkles of the hand are represented. Further, the print image 91 has clear borders between the portions of the bones of the hand and the other portions, shows no degradation in brightness and tone overall, and has good visibility.

The color printer 6 applies color conversion to medical image data in RGB format generated by an X-ray-based modality according to the K monochrome conversion method, thereby generating print image data in K format without degrading the brightness and tone of the medical image. Thereby, the color, printer 6 forms a monochrome medical image in the form of a high-quality monochrome print image on a paper medium 36 based on the print image data, preventing reduction in visibility of the print image.

On the other hand, for example, a non-X-ray-based modality sequentially reads a region to be diagnosed of a patient at predetermined intervals to generate a relatively great number of medical images as tomographic images at different positions of the human body. The multiple medical images generated by the non-X-ray-based modality each show not only a region to be diagnosed but also other regions as gray portions obtained by reading the region to be diagnosed, due to the nature of the tomographic images.

The number of medical images generated by the non-X-ray-based modality is relatively great. Thus, medical images to be printed to present a patient and other persons are selected from among the generated medical images as appropriate, and gray portions in the selected medical images are colored to desired colors to facilitate distinguishing between the region to be diagnosed and the other regions. Of the multiple medical images generated by the non-X-ray-based modality, the colored selected medical images are transmitted to the color printer 6 in the form of DICOM file data. Regarding the medical images generated by the non-X-ray-based modality, the personal computer 5 may perform the selection and coloring of the medical images to be presented, or the non-X-ray-based modality may perform the selection and coloring of the medical images to be presented when generating the multiple medical images, for example.

Thus, in the color printer 6, the CMYK color conversion method is assigned to medical image data in RGB format generated by the non-X-ray-based modalities. The color printer 6 applies color conversion to medical image data in RGB format generated by a non-X-ray based modality according to the CMYK color conversion method suitable for color conversion of a color image to generate print image data in CMYK format without degrading the brightness and tone of the medical image. Thereby, the color printer 6 forms a color medical image in the form of a high-quality color print image on a paper medium 36 based on the print image data, preventing reduction in visibility of the print image.

(1-5) Procedure of Image Forming Process

Figure 11:
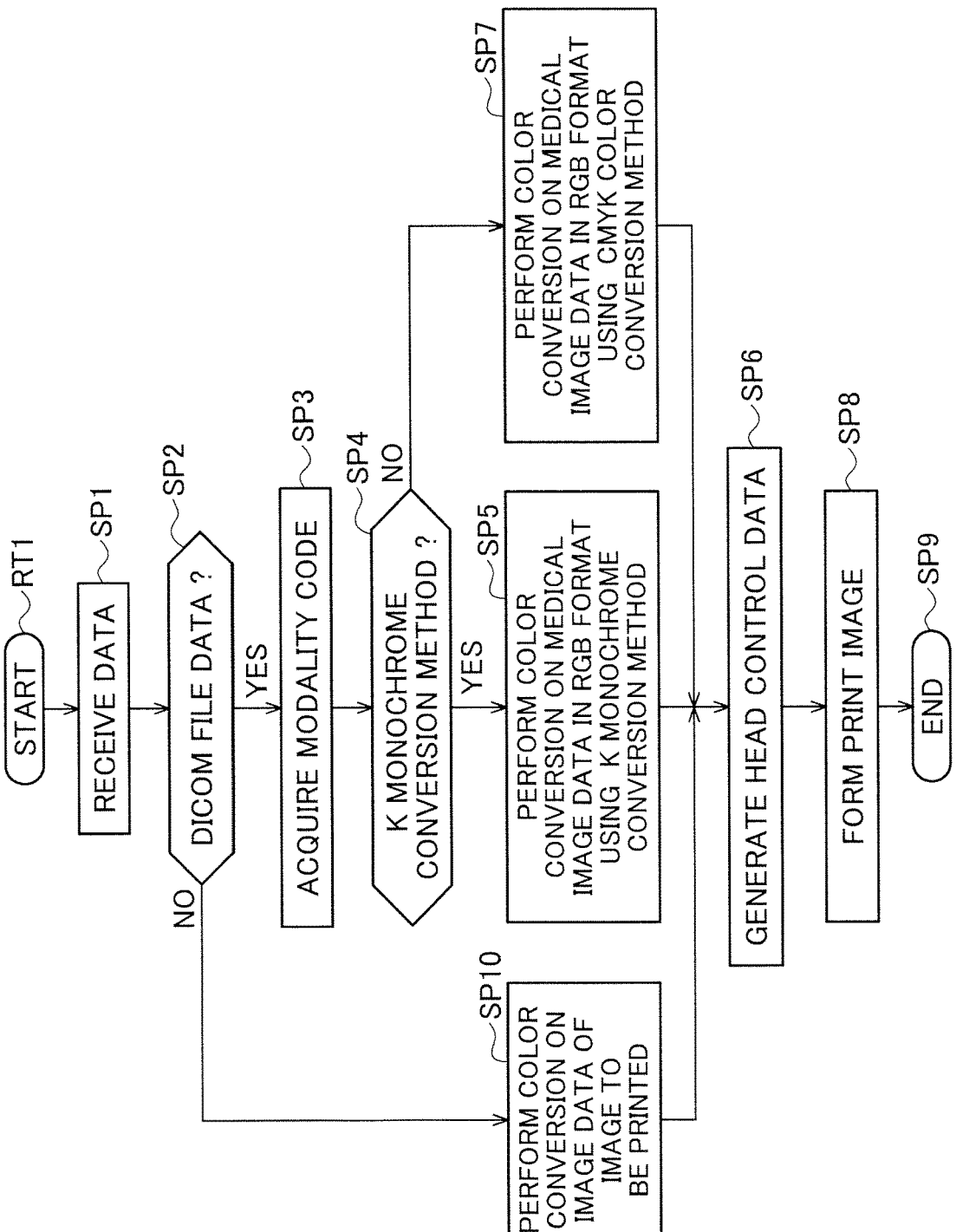
FIG. 11 is a flowchart illustrating an image processing procedure.

Next, an image processing procedure RT1 will be described with reference to the flowchart illustrated in FIG. 11. The image processing procedure RT1 is executed by the controller 70 of the color printer 6 in accordance with the image processing program previously stored in the storage unit 71. For example, when communication connection between the controller 70 and a modality 2, the image server 4 or the personal computer 5 via the network 3 is established, the controller 70 starts the image processing procedure RT1 illustrated in FIG. 11 in accordance with the image processing program. When starting the image processing procedure RT1, the controller 70 receives data (DICOM file data or print data) transmitted from the modality 2, image server 4, or personal computer 5 by the data receiver 72 in step SP1, and proceeds to step SP2.

In step SP2, the controller 70 determines whether the received data is DICOM file data. When the received data includes DICOM identification data and thus the controller 70 determines that the received data is DICOM file data (YES in step SP2), the controller 70 proceeds to step SP3. In step SP3, the controller 70 acquires the modality code from the DICOM file data, and proceeds to step SP4.

In step SP4, based on the modality code and the color conversion method determination table 80 stored in the storage unit 71, the controller 70 determines whether the color conversion method used for color conversion of the medical image data is the K monochrome conversion method. When the type of modality indicated by the modality code is the X-ray-based modality and the controller 70 determines that the color conversion method used for color conversion of the medical image data is the K monochrome conversion method (YES in step SP4), the controller 70 proceeds to step SP5. In step SP5, the controller 70 performs RGB-to-K color conversion on the medical image data in the DICOM file data based on the K color conversion table corresponding to the K monochrome conversion method to generate print image data in K format, then proceeding to step SP6.

On the other hand, when the type of modality indicated by the modality code is the non-X-ray-based modality and the controller 70 determines that the color conversion method used for color conversion of the medical image data the CMYK color conversion method (NO in step SP4), the controller 70 proceeds to step SP7. In step SP7, the controller 70 performs RGB-to-CMYK color conversion on the medical image data in the DICOM file data based on the CMYK color conversion table corresponding to the CMYK color conversion method to generate print image data in CMYK format, then proceeding to step SP6.

When the controller 70 generates the print image data in K format in step SP5, it generates one line of head control data based on the print image data in K format in step SP6, and then proceeds to step SP8. In step SP8, the controller 70 forms a monochrome medical image in the form of a monochrome print image on a surface of a paper medium 36 based on the one line of head control data, and then proceeds to step SP9 to end the image processing procedure RT1.

On the other hand, when the controller 70 generates the print image data in CMYK format in step SP7, it generates four lines of head control data based on the print image data in CMYK format in step SP6, and then proceeds to step SP8. In step SP8, rise controller 70 forms a color medical image in the form of a color print image on a surface of a paper medium 36 based on the four lines of head control data, and then proceeds to step SP9 to end the image processing procedure RT1.

When the received data includes no DICOM identification data and thus the controller 70 determines that the received data is print data (NO in step SP2), the controller 70 proceeds to step SP10.

When the image to be printed represented by the print data is monochrome, the controller 70 performs color conversion on the image to be printed based on the K color conversion table to generate print image data in K format in step SP10, and then proceeds to step SP6. In step SP6, the controller 70 generates one line of head control data based on the print image data in K format, and then proceeds to step SP8. In step SP8, the controller 70 forms the monochrome image to be printed in the form of a monochrome print image on a surface of a paper medium 36 based on the one line of head control data, and then proceeds to step SP9 to end the image processing procedure RT1.

On the other hand, when the image to be printed represented by the print data is color, the controller 70 performs color conversion on the image to be printed based on the CMYK color conversion table to generate print image data in CMYK format in step SP10, and then proceeds to step SP6. In step SP6, the controller 70 generates four lines of head control data based on the print image data in CMYK format, and then proceeds to step SP8. In step SP8, the controller 70 forms the color image to be printed in the form of a color print image on a surface of a paper medium 36 based on the four lines of head control data, and then proceeds to step SP9 to end the image processing procedure RT1.

(1-6) Operation and Advantages of Embodiment

In the above configuration, when the controller 70 of the color printer 6 receives data from the outside, it determines whether the received data is DICOM file data including medical image data. When it is determined that the received data is DICOM file data, the controller 70 acquires the modality code from the DICOM file data. The controller 70 of the color printer 6 determines, based on the modality code and color conversion method determination table 80, the color conversion method for color conversion to be applied to the medical image data. Depending on the determination of the color conversion method, the controller 70 of the color printer 6 performs color conversion on medical image data generated by an X-ray-based modality according to the K monochrome conversion method to generate print image data or performs color conversion on medical image data generated by a non-X-ray-based modality according to the CMYK color conversion method to generate print image data. The controller 70 of the color printer 6 then controls the image forming section 37 based on the print image data to form a medical image in the form of a print image on a surface of a paper medium 36.

With the above configuration, the color printer 6 can generate print image data while preventing degradation in brightness and tone of the medical image due to color conversion of medical image data generated by a modality 2, regardless of the type of the modality 2. Thereby, the color printer 6 can form a print image with good visibility on a surface of a paper medium 36 based on the medical image data, regardless of the type of the modality 2.

A comparative color printer performs RGB-to-CMYK color conversion on medical image data in RGB format generated by various modalities to generate print image data in CMYK format, regardless of the types of the modalities. For some types of modalities (e.g., X-ray-based modalities), the comparative color printer degrades the brightness or tone of medical images due to color conversion of medical image data generated by modalities and forms print images with poor visibility on surfaces of paper media. In contrast, the color printer 6 can generate print image data while preventing degradation in brightness and tone of medical images due to color conversion of medical image data generated by modalities, thereby forming print images with good visibility on surfaces of paper media based on the medical image data, regardless of the types of the modalities.

When the comparative color printer, which is the same as the color printer 6 except tor the color conversion, performs color conversion on medical image data generated by an X-ray-based modality according to the CMYK color conversion method to generate print image data and forms the print image 90 illustrated in FIG. 9, for example, the amount of the used black toner is 37.69%, the amount of the used cyan toner is 23.48%, the amount of the used magenta toner is 19.77%, and the amount of the used yellow toner is 18.79%, with the total amount of the toners used in the formation of the print image 90 as 100%. On the other hand, when the color printer 6 performs color conversion on the same medical image data generated by the X-ray-based modality according to the K monochrome conversion method to generate print image data and forms the print image 91 illustrated in FIG. 10, the amount of the used black toner is 48.17%, the amount of the used cyan toner is 0%, the amount of the used magenta toner is 0%, and the amount of the used yellow toner is with the total amount of the toners used in the formation of the print image 90 illustrated in FIG. 9 as 100%.

Thus, compared to the case where the comparative color printer performs color conversion on the medical image data generated by the X-ray-based modality according to the CMYK color conversion method, when the color printer 6 performs color conversion on the medical image data according to the K monochrome conversion method, the amount of the used black toner increases by about 10% and no toners of cyan, magenta, and yellow are used. Thus, the color printer 6 can reduce the amount of toner used in performing color conversion on medical image data generated by an X-ray-based modality to form a print image, as compared to the comparative color printer.

While the color printer 6 performs color conversion on medical image data generated by any type of modalities to generate print linage data and terms print, images, it changes the color conversion method for the color conversion applied to the medical image data, depending on the types of the modalities. This makes it possible to reduce the amount of toner used in the formation of the print images and improve convenience, as compared to the comparative color printer.

(2) Modifications (2-1) First Modification

In the above embodiment, the color printer 6 uses the two color conversion methods, but the color printer 6 may use three or more color conversion methods (or color conversion tables).

In the above embodiment, the color printer 6 performs color conversion on medical image data in RGB format according to one of the K monochrome conversion method and CMYK color conversion method depending on the type of the modality 2. However, the present invention is not limited to this. The color printer 6 may use a different color conversion method (or color conversion table) for each type of modality. For example, the color printer 6 may be configured as follows. For each type of modality, the color printer 6 basically performs RGB-to-K or RGB-to-CMYK color conversion on medical image data as in the above embodiment, but performs the color conversion according to a color conversion method having a different color profile (or color conversion table). This configuration makes it possible to, for each type of modality, perform color conversion on medical image data in RGB format according to a color conversion method having a color profile suitable for the color of the medical image and form a print image with good visibility on a paper medium 36, as con-spared to the embodiment described above.

(2-2) Second Modification

The color printer 6 may determine the color conversion method (or color conversion table) used for the color conversion depending on the modality code and the type of the paper medium 36. Also, the color printer 6 may change the color conversion method (or color conversion table) need for the color conversion depending on the type of the paper medium 36. For example, in the configuration of the first modification, the color printer 6 may change the color conversion table (or color conversion method) used for the color conversion of medical image data in RGB format of each type of modality, depending on the type of the paper medium 36 (a pure paper medium made without using used paper, a recycled paper medium, paper media having different thicknesses, paper media having different, colors, or the like) used for formation of a print image. This configuration makes it possible to, for each type of modality, perform color conversion on medical image data in RGB format according to a color conversion method having a color profile suitable for the color of the medical image and the type of the paper medium 36 and form a print image with good visibility on the paper medium 36, as compared to the embodiment described above.

(2-3) Third Modification

The DICOM standard specifies that the metadata section of DICOM file data can store, as an attribute of medical image data, tag data indicating whether the medical image data is color or monochrome. Each of the modalities 2 can operate as follows. When the modality 2 reads a region to be diagnosed of a patient, for example, to generate DICOM file data with medical image data representing a monochrome medical image, it can store tag data indicating monochrome in the metadata section; when the modality 2 colors the medical image, it can store tag data indicating color in the metadata section in place of the tag data indicating monochrome.

The color printer 6 may change the color conversion method used for the color conversion based on color information (e.g., whether the medical image data is color or monochrome) indicated by the tag data included in the DICOM file data. For example, after determining a color conversion method based on the modality code, the color printer 6 may determine a color conversion method based on color information indicated fey the tag data included in the DICOM file data, and perform color conversion according to the color conversion method determined based on the color information, instead of the color conversion method determined based on the modality code. For example, in a case where the color printer 6 receives DICOM file data generated by a non-X-ray-based modality, after the color printer 6 determines the CMYK color conversion method as the color conversion method based on the modality code and color conversion method determination table 80, it determines, based on the tag data, whether the medical image data is color or monochrome. When the color printer 6 determines that the medical image data is color, if performs color conversion on the medical image data according to the CMYK color conversion method, which has been determined based on the modality code and color conversion method determination table 80; when the color printer 6 determines that the medical image data is monochrome, it performs color conversion on the medical image data according to the K monochrome conversion method, instead of the CMYK color conversion method, which has been determined based on the modality code and color conversion method determination table 80. With this configuration, when the color printer 6 receives DICOM file data including medical image data that has been generated by a non-X-ray-based modality but has not been colored, the color printer 6 can perform color conversion on the medical image data according to the K monochrome conversion method, which is suitable tor color conversion of monochrome images, to generate print image data in K format without degrading the brightness and tone of the medical image, thereby providing a print Image with good visibility.

The above configuration can also be applied to medical image data generated by X-ray-based modalities. For example, in a case where the color printer 6 receives DICOM file data generated by an X-ray-based modality, after the color printer 6 determines the K monochrome conversion method as the color conversion method based on the modality code and color conversion method determination table 80, it determines, based on the tag data, whether the medical image data is color or monochrome. When the color printer 6 determines that the medical image data is monochrome, it performs color conversion on the medical image data according to the K monochrome conversion method, which has been determined based on the modality code and color conversion method determination table 80; when the color printer 6 determines that the medical image data is color, it performs color conversion on the medical image data according to the CMYK color conversion method, instead of the K monochrome conversion method, which has been determined based on the modality code and color conversion method determination table 80. With this configuration, when the color printer 6 receives DICOM file data including medical image data that has been generated by an X-ray-based modality but has been colored, the color printer 6 can perform color conversion on the medical image data according to the CMYK color conversion method, which is suitable for color conversion of color images, to generate print image data in CMYK format without degrading the brightness and tone of the medical image thereby providing a print image with good visibility.

Further, the color printer 6 may determine the color conversion method used for the color conversion depending on the color information instead of the modality code.

(2-4) Fourth Modification

In the above embodiment, the modalities 2 other than computed X-ray imaging devices, mammography devices, computed tomography devices, nuclear magnetic resonance tomography devices, and ultrasonic diagnostic devices are grouped into one group, and the color conversion method determination table 80 describes no corresponding modality code 82 and describes only color conversion method information 83 in association with the group. However, the present invention is not limited to this. For each of the types of all the modalities 2 capable of communicating with the color printer 6 and all the modalities 2 incapable of directly communicating with the color printer 6 but capable of generating medical image data that the color printer 6 can acquire via the personal computer 5 or image server 4, the color conversion method determination table 80 may describe the device name data 81, modality code 82, and color conversion method information 83 in association with each other. Moreover, when a modality 2 capable of communicating with the color printer 6 or a modality 2 incapable of directly communicating with the color printer 6 but capable of generating medical image data that the color printer 6 can acquire via the personal computer 5 or image server 4 is added, the color conversion method determination table 80 may be updated by adding thereto the device name data 81, modality code 82, and color conversion method information 83 for the type of the added modality 2.

(2-5) Fifth Modification

In the above embodiment, the controller 70 of the color printer 6 executes the image processing procedure RT1 described with reference to FIG. 11 in accordance with the image processing program previously stored in the storage unit 71. However, the present invention is not limited to this. The controller 70 of the color printer 6 may execute the image processing procedure RT1 by installing an image processing program from a computer-readable storage medium storing the image processing program or installing an image processing program from the outside through a wired or wireless communication medium, such as a local area network, the Internet, or digital satellite broadcasting. The computer-readable storage medium for installing the image processing program in the color printer 6 so that the color printer 6 can execute the image processing program may be a package medium, such as a flexible disk, a compact disc-read only memory (CD-ROM), or a digital versatile disc (DVD), or may be a semiconductor memory, a magnetic disc, or the like storing the image processing program temporarily or permanently. To store the image processing program in a computer-readable storage medium, a wired or wireless communication medium, such as s local area network, the Internet, or digital, satellite broadcasting, may be used. Also, the image processing program may be stored in a computer-readable storage medium through a router, a modem, or other various communication interfaces.

(2-6) Sixth Modification

In the above embodiment, the present invention is applied to the color printer 6 described with reference to FIGS. 1 to 11. However, the present invention is not limited to this. The present invention is widely applicable to various image forming apparatuses, such as multi-function peripherals (MFPs). In the above embodiment, the controller 70 of the color printer 6 executes the image processing procedure RT1 as an image processing method of the present invention in accordance with the image processing program. An information processing apparatus, such as the personal computer 5 or a tablet terminal, may execute the processes of steps SP1 to SP5 and SP7 in the image processing procedure RT1 as the image processing method of the present invention by a printer driver stored in a storage unit to obtain print image data and transmit the obtained print image data to an image forming apparatus, such as the color printer 6 or an MFP.

The present invention is applicable to image forming apparatuses, such as color printers or MFPs.

The present invention is not limited to the embodiment and modifications described above; it can be practiced in various other aspects without departing from the inventive scope.

What is claimed is:

1. An information processing apparatus comprising:
   a storage unit that stores color conversion method determination information in which for each of a plurality of types of modalities that each generate medical information data including medical image data and modality type data indicating the type of the modality, color conversion method information is associated with modality type data indicating the type of modality, the plurality of types of modalities including first and second types of modalities, the color conversion method information for the first type of modality indicating a first color conversion method, the color conversion method information for the second type of modality indicating a second color conversion method;
   a data receiver that receives data;
   a data acquisition unit that, when the data received by the data receiver is medical information data, acquires the modality type data from the received medical information data;
   a method determiner that determines, based on the modality type data acquired by the data acquisition unit and the color conversion method determination information stored in the storage unit, the color conversion method for the medical image data included in the received medical information data, the method determiner determining, as the color conversion method for the received medical image data, the first color conversion method when the acquired modality type data indicates the first type of modality and the second color conversion method when the acquired modality type data indicates the second type of modality; and
   a color converter that performs color conversion on the medical image data according to the color conversion method determined by the method determiner to generate print image data, the color converter performing the color conversion on the medical image data according to the first color conversion method to generate monochrome image data as the print image data when the acquired modality type data indicates the first type of modality, the color converter performing the color conversion on the medical image data according to the second color conversion method to generate multicolor image data as the print image data when the acquired modality type data indicates the second type of modality.

2. The information processing apparatus of claim 1, wherein the medical information data conforms to DICOM standard.

3. The information processing apparatus of claim 1, further comprising a data determiner that determines whether the data received by the data receiver is medical information data,
   wherein when the data determiner determines that the received data is medical information data, the data acquisition unit acquires the modality type data from the received medical information data.

4. The information processing apparatus of claim 1, wherein:
   the first type of modality generates the medical image data using X-rays; and
   the second type of modality generates the medical image data without using X-rays.

5. The information processing apparatus of claim 4, wherein the color converter:
   when the modality type data acquired from the received medical information data indicates the first type of modality, performs the color conversion on the medical image data based on monochrome conversion information to generate the print image data; and
   when the modality type data acquired from the received medical information data indicates the second type of modality, performs the color conversion on the medical image data based on multicolor conversion information to generate the print image data.

6. The information processing apparatus of claim 4, wherein the first and second color conversion methods use different color conversion tables for color conversion of medical image data, and
   wherein the color converter:
   when the modality type data acquired from the received medical information data indicates the first type of modality, performs the color conversion on the medical image data based on one of the color conversion tables corresponding to the first color conversion method to generate the monochrome image data as the print image data; and
   when the modality type data acquired from the received medical information data indicates the second type of modality, performs the color conversion on the medical image data based on one of the color conversion tables corresponding to the second color conversion method to generate the multicolor image data as the print image data.

7. The information processing apparatus of claim 1, wherein the information processing apparatus changes the color conversion method used for the color conversion based on color information indicated by tag data included in the received medical information data.

8. The information processing apparatus of claim 1, wherein the color conversion method determination information is updatable.

9. The information processing apparatus of claim 1, wherein the information processing apparatus is an image forming apparatus that forms an image on a medium based on the generated print image data.

10. The information processing apparatus of claim 9, wherein the information processing apparatus changes the color conversion method used for the color conversion depending on a type of the medium.

11. The information processing apparatus of claim 1, wherein the information processing apparatus is configured to be connected to an image forming apparatus capable of multicolor printing.

12. The information processing apparatus of claim 11, wherein the information processing apparatus is a personal computer comprising a printer driver that functions as the color converter.

13. The information processing apparatus of claim 1, wherein the monochrome image data is image data of black, and the multicolor image data is image data of cyan, magenta, yellow, and black.

14. An image processing method comprising:
receiving data;
acquiring, when the received data is medical information data generated by a modality and including medical image data, modality type data indicating a type of the modality from the received medical information data;
determining, based on the acquired modality type data and color conversion method determination information in which for each of a plurality of types of modalities that each generate medical information data including medical image data, color conversion method information indicating a color conversion method for the medical image data is associated with modality type data indicating the type of modality, the color conversion method for the medical image data included in the received medical information data; and
performing color conversion on the medical image data according to the determined color conversion method to generate print image data,
wherein the plurality of types of modalities include first and second types of modalities, the color conversion method information for the first type of modality indicates a first color conversion method, and the color conversion method information for the second type of modality indicates a second color conversion method, and
wherein the determining determines, as the color conversion method for the received medical image data, the first color conversion method when the acquired modality type data indicates the first type of modality and the second color conversion method when the acquired modality type data indicates the second type of modality, and
wherein the performing performs the color conversion on the medical image data according to the first color conversion method to generate monochrome image data as the print image data when the acquired modality type data indicates the first type of modality, and performs the color conversion on the medical image data according to the second color conversion method to generate multicolor image data as the print image data when the acquired modality type data indicates the second type of modality.

15. The image processing method of claim 14, wherein the medical information data conforms to DICOM standard.

16. The image processing method of claim 14, further comprising determining whether the received data is medical information data,
wherein when it is determined that the received data is medical information data, the acquiring acquires the modality type data from the received medical information data.

17. The image processing method of claim 14, further comprising changing the color conversion method used for the color conversion based on color information indicated by tag data included in the received medical information data.

18. The image processing method of claim 14, wherein the color conversion method determination information is updatable.

19. The image processing method of claim 14, further comprising forming an image on a medium based on the generated print image data.

20. The image processing method of claim 19, further comprising changing the color conversion method used for the color conversion depending on a type of the medium.

21. The image processing method of claim 14, wherein the image processing method is performed by a personal computer.

22. The image processing method of claim 21, wherein the color conversion is performed by a printer driver of the personal computer.

23. The information processing apparatus of claim 14, wherein the monochrome image data is image data of black, and the multicolor image data is image data of cyan, magenta, yellow, and black.

* * * * *